United States Patent
Gibbons

[11] 3,936,638
[45] Feb. 3, 1976

[54] RADIOLOGY

[75] Inventor: David John Gibbons, Ickenham, England

[73] Assignee: EMI Limited, Hayes, England

[22] Filed: June 26, 1974

[21] Appl. No.: 483,451

[30] Foreign Application Priority Data
July 6, 1973 United Kingdom............... 32422/73

[52] U.S. Cl.............. 250/358 R; 250/312; 250/370
[51] Int. Cl.². ..................... G01N 23/00; G01T 1/22
[58] Field of Search ........... 250/364, 358, 312, 460, 250/370, 320, 323

[56] References Cited
UNITED STATES PATENTS

| | | | |
|---|---|---|---|
| 3,207,902 | 9/1965 | Sandborg | 250/370 |
| 3,396,318 | 8/1968 | Chow | 250/370 |
| 3,769,507 | 10/1973 | Kenney et al. | 250/460 |
| 3,809,904 | 5/1974 | Clarke et al. | 250/312 |

Primary Examiner—Harold A. Dixon
Attorney, Agent, or Firm—Fleit & Jacobson

[57] ABSTRACT

In a method of investigating a body of means of penetrating radiation such as X- or γ- radiation, the energy of the radiation is chosen to be such that the radiation is scattered, rather than absorbed, by the body. The scattered radiation is detected by means of banks of detector means disposed on the opposite side of the body to the source, and the detector means include energy analyzing means to enable the angle of incidence thereon of scattered radiation to be determined.

3 Claims, 1 Drawing Figure

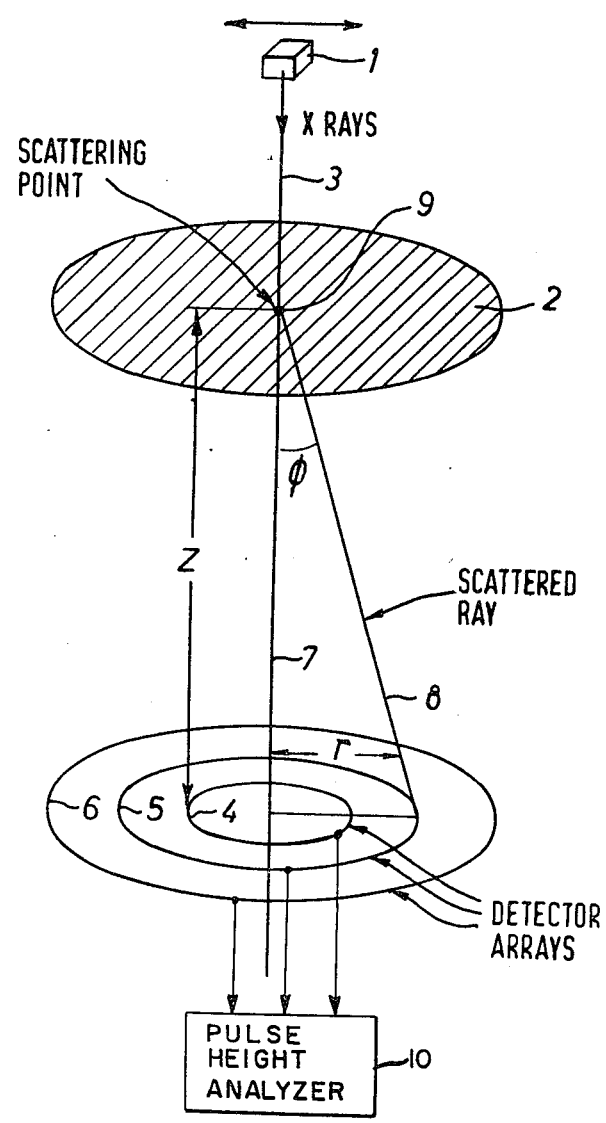

RADIOLOGY

The present invention relates to radiology, and it relates especially to the kind of radiological apparatus and method in which a tomographic section of a body is investigated using radiation of energy in the range 0.2 MeV to 2.0 MeV. In this energy range, the radiation tends to be scattered, rather than absorbed, by the body and if the radiation is directed into the body from a known direction along a thin "pencil" beam, or ray as it might be called, then the direction of emergence of the radiation from the body can be monitored and used to determine the positions of scatter centres within the body. The direction of emergence is conveniently monitored by means of a plurality of detectors disposed in concentric rings centred on the axis of the pencil beam, and the beam and detectors are scanned synchronously relative to the body so as to permit said tomographic section to be examined.

The detection of the angle of incidence of the scattered radiation can be associated with some difficulty and it is an object of this invention to provide a radiological apparatus and method in which this difficulty is reduced.

According to the invention from one aspect there is provided a method of examining a body by means of penetrating radiation such as X- or γ- radiation, the energy of the radiation being such that it tends to be scattered by, rather than absorbed by, the body, including the steps of:

a. directing said radiation in the form of a pencil like beam into said body,
b. defining at least one annular detection region arranged concentric to said beam in a plane which is intersected substantially normally by the beam,
c. detecting radiation incident, after passage through the body, on at least one of siad regions,
d. monitoring the energy of said detected radiation,
e. correlating the monitored value of the energy with the radius of the detection region on which the radiation was incident so as to determine the path taken by that radiation through the body and
f. repeating steps (b), (c), (d) and (e) while said radiation is directed into the body from different dispositions relative thereto.

According to the invention from another aspect there is provided apparatus for examining a body by means of radiation such as X- or γ- radiation, including a source of a beam of radiation of energy in the range 0.2 to 2.0 MeV, means for directing said radiation into said body, a detecting arrangement disposed on the opposite side of said body to said source, the detecting arrangement comprising a plurality of arrays of detectors, arranged in circles concentric about the said beam, and means associated with said detectors for determining the energy of radiation detected thereby.

In order that the present invention may be clearly understood and readily carried into effect, one embodiment thereof will not be described, by way of example only, with reference to the accompanying drawing, the single FIGURE of which shows, in schematic form, apparatus in accordance with one example of the invention.

Referring to the drawing, a source 1 of penetrating radiation, in this case X-radiation, is arranged to irradiate a body 2 along a thin pencil beam 3. The energy of the radiation is arranged to be such that the radiation tends to be scattered rather than absorbed by the body and in this example the energy of the radiation lies in the range from 0.2 MeV to 2.0 MeV.

Disposed in a plane on the opposite side of the body 2 to the source 1 are three circular arrays of radiation sensitive detectors 4, 5 and 6; the arrays being concentric about the produced line 7 of the beam 3, the latter intersecting at right angles the plane of the detectors. Each array of detectors is such as to be capable of measuring the energy of the radiation received thereby.

Thus the extent to which a scattered ray such as 8 has been deviated from the straight-through path 7 is known by virtue of which of the arrays of detectors it is incident upon. Moreover the energy of the radiation in the scattered ray such as 8 is known. This latter knowledge can be used to determine the angle $\phi$ between the straight-through path 7 and the scattered ray 8 — which will depend upon the position of the scattering point 9 within the body 2 — by virtue of the well known Compton scattering formula:

$$\Delta \lambda = 0.024 (1 - \cos \phi)$$

which relates the change in wavelength (and hence change in energy) between the scattered ray 8 and the input pencil beam 3. Thus, by using suitable pulse-height analysers 10 associated with the detector arrays, it is possible to measure the energy accurately and so to compute $\phi$ and therefore the distance Z of the scattering point 9 along the axis 3, 7.

Suitable energy discriminating detectors are lithium — drifted silicon, lithium — drifted gemanium or cadmium tellurium. An accuracy of up to 1 : 1000 is possible using commercially available detectors of this kind, and techniques well known in the art.

What I claim is:

1. Apparatus for examining a body by means of radiation such as X- or γ- radiation, including a source of a beam of radiation of energy in the range 0.2 to 2.0 MeV, means for directing said radiation into said body, a detecting arrangement disposed on the opposite side of said body to said source, the detecting arrangement comprising a plurality of arrays of detectors, arranged in circles concentric about the said beam, and means associated with said detectors for determining the energy of radiation detected thereby.

2. Apparatus according to claim 1 wherein said means associated with said detector comprises one of the following materials:
   i. lithium drifted silicon
   ii. lithium drifted gemanium and
   iii. cadmium tellurium.

3. A method of examining a body by means of penetrating radiation such as X- or γ- radiation, the energy of the radiation being such that it tends to be scattered by, rather than absorbed by, the body, including the steps of:

a. directing said radiation in the form of a pencil like beam into said body,
b. defining at least one annular detection region arranged concentric to said beam in a plane which is intersected substantially normally by the beam,
c. detecting radiation incident, after passage through the body, on at least one of said regions,
d. monitoring the energy of said detected radiation,
e. correlating the monitored value of the energy with the radius of the detection region on which the radiation was incident so as to determine the path taken by that radiation through the body and f. repeating steps (b), (c), (d) and (e) while said radiation is directed into the body from different dispositions relative thereto.

* * * * *